(12) United States Patent
Vlielander et al.

(10) Patent No.: US 10,815,466 B2
(45) Date of Patent: Oct. 27, 2020

(54) MILDEW RESISTANCE GENE IN KALANCHOE

(71) Applicant: Dümmen Group B.V., De Lier (NL)

(72) Inventors: Izaak Johannes Vlielander, De Lier (NL); Chunting Lang, De Lier (NL); Paulus Cornelis Maris, De Lier (NL); Roger Adrianus Peeters, Weert (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/553,199

(22) PCT Filed: Feb. 29, 2016

(86) PCT No.: PCT/EP2016/054220
§ 371 (c)(1),
(2) Date: Aug. 24, 2017

(87) PCT Pub. No.: WO2016/139178
PCT Pub. Date: Sep. 9, 2016

(65) Prior Publication Data
US 2018/0037875 A1    Feb. 8, 2018

(30) Foreign Application Priority Data

Mar. 4, 2015   (EP) .................................. 15157519

(51) Int. Cl.
*C12N 15/82*    (2006.01)
*C12N 9/16*    (2006.01)

(52) U.S. Cl.
CPC ........... *C12N 9/16* (2013.01); *C12N 15/8282* (2013.01); *C12Y 301/02* (2013.01)

(58) Field of Classification Search
CPC ....................................................... C12N 9/16
USPC ....................................................... 800/279
See application file for complete search history.

(56) References Cited

U.S. PATENT DOCUMENTS

| PP6,878 P | 6/1989 | Finger |
| PP13,355 P2 | 12/2002 | Rosborg |
| PP18,030 P3 * | 9/2007 | Jepsen ..................... A01H 6/32 |
| 2007/0061916 A1 * | 3/2007 | Kovalic ............... C07K 14/415 |
| | | 800/278 |

FOREIGN PATENT DOCUMENTS

NL    2013042 A    11/2014

OTHER PUBLICATIONS

GenBank Accession No. KDP24210.1 (2014).*
Third Party Observation submitted in European Patent Application No. 15157519.8, dated Jan. 6, 2020.*
Database UniProt [Online] Sep. 3, 2014 (Sep. 3, 2014), "SubName: Full=Uncharacterized protein {EC0:0000313:EMBL:KDP24210.1};" XP002743885, 1,2, 7-11, 13-16,18 retrieved from EBI accession No. UNIPROT: AOA067JW66 Database accession No. AOA067JW66 sequence.
Song et al., "Overexpresion of a wheat stearoyl-ACP desaturase (SACPD) gene TaSSI2 in *Arabidopsis* ssi2 mutant compromise its resistance to powdery mildew", Gene, 2013, pp. 220-227, vol. 524.
Tang et al., "Mutations in LACS2, a Long-Chain Acyl-Coenzyme A Synthetase, Enhance Susceptibility to Avirulent Pseudomonas syringae But Confer Resistance to Botrytis cinerea in *Arabidopsis*", Plant Physiology, 2007, pp. 1093-1103, vol. 144.
Third Party Observations submitted in European Patent Application No. 15157519.8, dated Jan. 6, 2020.

* cited by examiner

*Primary Examiner* — Li Zheng
(74) *Attorney, Agent, or Firm* — The Webb Law Firm (57) ABSTRACT

Provided herein are proteins capable of providing a mildew resistant phenotype, or mildew resistance, to plants belonging to the *Kalanchoe* genus. Also provided herein are nucleic acid sequences, or cDNA sequences, and genes encoding the present proteins. Further provided herein are methods using the proteins, nucleic acid sequences and genes for selecting mildew resistant *Kalanchoe* plants, such as *Oidium kalanchoeae* resistant *Kalanchoe* plants, and to generate mildew resistant *Kalanchoe* plants, such as *Oidium kalanchoeae* resistant *Kalanchoe* plants, comprising the present proteins, mRNA forms of the present cDNAs or the present genes.

9 Claims, 2 Drawing Sheets

Specification includes a Sequence Listing.

Figure 1

```
Query    1    MRSGTICVINGKCGSIHRPATAAESTSKKSNTPLTHRSNSDRSLMDLEAVKQLLEKGDSE    60
              MRSGTICVINGKCGSIHRPAT   ESTSKKSNTPLTHRSNSDRSLMDLEAVKQLLEKGDSE
Sbjct    1    MRSGTICVINGKCGSIHRPATTTESTSKKSNTPLTHRSNSDRSLMDLEAVKQLLEKGDSE    60

Query   61    SQQAIDSMRSRFFEPFMMAGLKVERVEPGRLICSMKVPARLLNAGGFLHGGATATLVDLV   120
              SQQAIDSMRSRFFEPFMMAGLKVERVEPGRLICSMKVPARLLNAGGFLHGGATATLVDLV
Sbjct   61    SQQAIDSMRSRFFEPFMMAGLKVERVEPGRLICSMKVPARLLNAGGFLHGGATATLVDLV   120

Query  121    GSAAIFTAGATVTGVSVEISVSYLDAAFEGEEVEIEARVLRVGKAVGVVSVEIRKKGSGK   180
              GSAAIFTAGATVTGVSVEISVSYLDAAFEGEEVEIEARVLRVGKAVGVVSVEIRKKGSGK
Sbjct  121    GSAAIFTAGATVTGVSVEISVSYLDAAFEGEEVEIEARVLRVGKAVGVVSVEIRKKGSGK   180

Query  181    IVAQGRHTKYLAVASKL   197
              IVAQGRHTKYLAVASKL
Sbjct  181    IVAQGRHTKYLAVASKL   197
```

Figure 2

MILDEW RESISTANCE GENE IN KALANCHOE

CROSS-REFERENCE TO RELATED APPLICATIONS

This application is the United States national phase of International Application No. PCT/EP2016/054220 filed Feb. 29, 2016, and claims priority to European Patent Application No. 15157519.8 filed Mar. 4, 2015, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1707302_ST25.txt. The size of the text file is 9,362 bytes, and the text file was created on Aug. 16, 2017.

The present invention relates to proteins capable of providing a mildew resistant phenotype, or mildew resistance, to plants belonging to the *Kalanchoe* genus. The present mildew resistance is preferably a resistance against mildew infections wherein *Oidium kalanchoeae* is the causative pathogen. The present invention also relates to nucleic acid sequences, or cDNA sequences, and genes encoding the present proteins. The present invention further relates to use of the present proteins, nucleic acid sequences and genes for selecting mildew resistant *Kalanchoe* plants, such as *Oidium kalanchoeae* resistant *Kalanchoe* plants, and to mildew resistant *Kalanchoe* plants, such as *Oidium kalanchoeae* resistant *Kalanchoe* plants, comprising the present proteins, mRNA forms of the present cDNAs or the present genes.

*Kalanchoe* is a genus of about 125 species of tropical, succulent flowering plants in the family Crassulaceae. Only one species of this genus is known to originate from the Americas, 56 from southern & eastern Africa and 60 species from Madagascar. *Kalanchoe* plants are also found in southeastern Asia and China.

Known species belonging to the *Kalanchoe* genus are *Kalanchoe adelae; Kalanchoe arborescens, Kalanchoe beauverdii, Kalanchoe beharensis, Kalanchoe bentii, Kalanchoe blossfeldiana Kalanchoe bouvetii, Kalanchoe bracteata, Kalanchoe campanulata, Kalanchoe crenata, Kalanchoe crundallii, Kalanchoe daigremontiana, Kalanchoe delagoensis, Kalanchoe dinklagei, Kalanchoe eriophylla, Kalanchoe farinacea, Kalanchoe fedtschenkoi, Kalanchoe figuereidoi, Kalanchoe flammea, Kalanchoe gastonis, Kalanchoe glaucescens, Kalanchoe gracilipes, Kalanchoe grandidieri, Kalanchoe grandiflora, Kalanchoe hildebrantii, Kalanchoe jongmansii, Kalanchoe kewensis, Kalanchoe laciniata, Kalanchoe laetivirens, Kalanchoe lateritia, Kalanchoe laxiflora, Kalanchoe linearifolia, Kalanchoe longiflora, Kalanchoe luciae, Kalanchoe macrochlamys, Kalanchoe manginii, Kalanchoe marnieriana, Kalanchoe marmorata, Kalanchoe millottii, Kalanchoe miniata, Kalanchoe nyikae, Kalanchoe obtusa, Kalanchoe orgyalis, Kalanchoe peltata, Kalanchoe petitiana, Kalanchoe pinnata, Kalanchoe porphyrocalyx, Kalanchoe prolifera, Kalanchoe pubescens, Kalanchoe pumila, Kalanchoe quartiniana, Kalanchoe rhombopilosa, Kalanchoe robusta, Kalanchoe rolandi, Kalanchoe rosei, Kalanchoe rotundifolia, Kalanchoe schizophylla, Kalanchoe serrata, Kalanchoe sexangularis, Kalanchoe streptantha, Kalanchoe suarezensis, Kalanchoe synsepala, Kalanchoe synsepala f. dissecta, Kalanchoe thyrsiflora, Kalanchoe tomentosa, Kalanchoe tubiflora, Kalanchoe uniflora, Kalanchoe velutina* and *Kalanchoe viguieri.*

Most *Kalanchoe* plants are shrubs or perennial herbaceous plants, but a few are annual or biennial. The largest plant, *Kalanchoe beharensis* from Madagascar can reach 6 meters but most species are less than 1 meter. *Kalanchoe* plants are characterized by opening their flowers through growing new cells on the inner surface of the petals to force them outwards and on the outside of the petals to close them.

*Kalanchoe* plants are generally cultivated as ornamental houseplants and rock or succulent garden plants. *Kalanchoe* plans are popular because of their ease of propagation, low water requirements, and wide variety of flower colors typically borne in clusters well above the vegetative growth. The section *Bryophyllum*—formerly an independent genus— contains species such as the "Air plant" *Kalanchoe pinnata*. In these plants, new individuals develop vegetatively as plantlets, also known as bulbils or gemmae, at indents along the leaves. These young plants eventually drop off and root. No males have been found in species of this genus which does flower and produce seeds and is commonly designated as the Mother of Thousands.

In common with other Crassulaceae (such as the genera *Tylecodon, Cotyledon* and *Adromischus*), some *Kalanchoe* species contain bufadienolide cardiac glycosides which can cause cardiac poisoning, particularly in grazing animals. This is a particular problem in the native range of many *Kalanchoe* species in the Karoo region of South Africa, where the resulting animal disease is known as krimpsiekte (shrinking disease) or cotyledonosis. Similar poisonings have also occurred in Australia.

In traditional medicine, *Kalanchoe* species have been used to treat ailments such as infections, rheumatism and inflammation. *Kalanchoe* extracts also have immunosuppressive effects. *Kalanchoe pinnata* has been recorded in Trinidad and Tobago as being used as a traditional treatment for hypertension.

Mildew disease manifests itself as a thin, superficial, usually whitish growth consisting of minute hyphae (fungal filaments) produced especially on living plants. In horticulture, mildew is a disease generally caused a by fungus belonging to the order *Erysiphales*. The name 'mildew' can also be used more generally to mean mold growth. In the art, mildew is also designated as powdery mildew and the terms mildew and powdery mildew are interchangeably used herein.

*Kalanchoe* is especially susceptible to mildew. Although mildew generally is not harmful to the growth of the plant, it does cause the plant to become unsightly and unattractive and thereby incurring significant economical losses for plant breeders.

The primary symptom of a mildew infection in *Kalanchoe* is the presence of a white talcum powder-like growth on leaves, buds, stems, new shoots and flowers. Mildew fungi prefer to infect young, tender leaves but will infect older leaves as well. Other symptoms associated with mildew include leaf yellowing, leaf necrosis, leaf rolling, distortion of leaves and premature leaf drop. *Kalanchoe* infected with mildew often become stunted. A severe mildew infection can eventually cover the entire plant. Preventing a mildew infection can be accomplished through cultural control methods or fungicides.

Both culture based methods and fungicides to control mildew in *Kalanchoe* have disadvantages. For example, culture based methods are not practical for commercial growth and culture of *Kalanchoe* plants and the disadvantages of fungicides are commonly known such as their impact on the environment and the development of resistant mildew pathogens due to selective pressure by the fungicide.

Considering the economical impact of a mildew infection, there is a continuing need in the art of *Kalanchoe* breeding for mildew resistant *Kalanchoe* plants and especially *Kalanchoe* plants being resistant tot the mildew pathogen *Oidium kalanchoeae*. In the art, *Oidium kalanchoeae*, *Oidium kalanchoeae* is also designated *Oidium kalanchoës* or *Oidium calanchoeae*.

It is an object of the present invention, amongst other objects, to meet the above need of the art.

The above object, amongst other objects, is met by the present invention through providing mildew, or powdery mildew, resistance genes encoding mildew resistance providing thioesterase or thioesterase-like proteins.

Specifically, the above object, amongst other objects and according to a first aspect, is met by the present invention through providing proteins comprising one or more amino acid substitutions, deletions or insertions in a thioesterase, or thioesterase-like protein, of a *Kalanchoe* plant as compared the protein of SEQ ID No. 1, or proteins having 80% sequence identity therewith, wherein the one or more amino acid substitutions, deletions or insertions provide an increased mildew resistance in a *Kalanchoe* plant as compared to a *Kalanchoe* plant comprising SEQ ID No. 1, or proteins having 80% sequence identity therewith.

The proteins described herein can be designated as ROK-1 proteins for being the first proteins identified providing mildew resistance and especially resistance to the mildew pathogen *Oidium kalanchoeae*.

The present increased mildew resistance, and especially the present resistance to *Oidium kalanchoeae*, is observed irrespective whether the encoding genes are homozygously or heterozygously present.

Within the context of the present invention, sequence identity percentages of 80% to 99% are contemplated such as 81%, 85%, 90%, 91%, 92%, 93%, 94%, 95%, 96%, 97% or 98%, under the condition that the corresponding protein provides mildew resistance in *Kalanchoe* plants.

As used herein, sequence identity, after suitable alignment, indicates the percentage identical amino acids or nucleic acids, over the entire length of SEQ ID No. 1 or SEQ ID No. 3, respectively.

According to an especially preferred embodiment of this aspect of the present invention, the present protein comprises one or more amino acid substitutions, deletions or insertions in amino acids 1 to 50 of SEQ ID No. 1. The present inventors have surprisingly discovered that the present mildew resistant phenotype, such as resistance to the mildew pathogen *Oidium kalanchoeae*, is especially provided through modification of the N-terminal region of SEQ ID No. 1. The present invention preferably relates to amino acid substitutions at position 22 and/or position 23 of SEQ ID No. 1, more preferably substitution of the amino acid threonine at position 22 and/or 23 of SEQ ID No. 1, most preferably substitution of the amino acid threonine with the amino acid alanine at position 22 and/or 23 of SEQ ID No. 1.

According to yet another especially preferred embodiment of the present invention, the amino acid sequence of the present protein is the amino acid sequence as shown in SEQ ID No. 2.

According to a most preferred embodiment, the proteins according to the present invention comprise the amino acid sequence motif "PATAAEST". In comparison, a protein not providing mildew resistance comprises, for example, the amino acid sequence motif "PATTTEST".

According to a preferred embodiment of this first aspect of the present invention, the present *Kalanchoe* plant is selected from the group consisting of *Kalanchoe adelae, Kalanchoe arborescens, Kalanchoe beauverdii, Kalanchoe beharensis, Kalanchoe bentii, Kalanchoe blossfeldiana, Kalanchoe bouvetii, Kalanchoe bracteata, Kalanchoe campanulata, Kalanchoe crenata, Kalanchoe crundallii, Kalanchoe daigremontiana, Kalanchoe delagoensis, Kalanchoe dinklagei, Kalanchoe eriophylla, Kalanchoe farinacea, Kalanchoe fedtschenkoi, Kalanchoe figuereidoi, Kalanchoe flammea, Kalanchoe gastonis, Kalanchoe glaucescens, Kalanchoe gracilipes, Kalanchoe grandidieri, Kalanchoe grandiflora, Kalanchoe hildebrantii, Kalanchoe jongmansii, Kalanchoe kewensis, Kalanchoe laciniata, Kalanchoe laetivirens, Kalanchoe lateritia, Kalanchoe laxiflora, Kalanchoe linearifolia, Kalanchoe longiflora, Kalanchoe luciae, Kalanchoe macrochlamys, Kalanchoe manginii, Kalanchoe marnieriana, Kalanchoe marmorata, Kalanchoe millottii, Kalanchoe miniata, Kalanchoe nyikae, Kalanchoe obtusa, Kalanchoe orgyalis, Kalanchoe peltata, Kalanchoe petitiana, Kalanchoe pinnata, Kalanchoe porphyrocalyx, Kalanchoe prolifera, Kalanchoe pubescens, Kalanchoe pumila, Kalanchoe quartiniana, Kalanchoe rhombopilosa, Kalanchoe robusta, Kalanchoe rolandi, Kalanchoe rosei, Kalanchoe rotundifolia, Kalanchoe schizophylla, Kalanchoe serrata, Kalanchoe sexangularis, Kalanchoe streptantha, Kalanchoe suarezensis, Kalanchoe synsepala, Kalanchoe synsepala f. dissecta, Kalanchoe thyrsiflora, Kalanchoe tomentosa, Kalanchoe tubiflora, Kalanchoe uniflora, Kalanchoe velutina* and *Kalanchoe viguieri*; preferably decorative flowering *Kalanchoe* plants selected from the group consisting of *K. blossfeldiana, K. laciniata, K. rotundifolia, K. aromatica, K. pubescens, K. grandiflora, K. citrina, K. ambolensis, K. faustii, K. schumacherii, K. pritwitzii, K. flammea, K. figueredoi, K. rauhii, K. obtusa, K. pumila, K. marmorata, K. porphyrocalux, K. jongmansii, K. pinnata, K. diagremontiana, K. gracilipes, K. campanulata, K. latisepela, K. coccinea, K. fedtschenkoi, K. tubiflora, K. decumbens, K. manginii, K. orgyalis, K. crenata, K. tomentosa* and hybrids thereof.

According to a second aspect, the present invention relates to nucleic acid sequences encoding the present proteins, preferably the present nucleic acids sequences have a nucleic acid substitution at position 64, and/or 67 of SEQ ID No. 3 such as a substitution of A with G, more preferably the present nucleic acid sequences have a sequence as depicted in SEQ ID No. 4 or SEQ ID No. 5 or SEQ ID No. 6.

According to a third aspect, the present invention relates to genes capable of being transcribed into the present nucleic acid sequences and the present proteins. Accordingly, the present invention encompasses genes capable of, under appropriate conditions, being a template for transcribing mRNA which mRNA is subsequently translated into the present protein sequences.

According to a fourth aspect, the present invention relates to the use of the present proteins, nucleic acid sequences or genes for selecting a mildew resistant *Kalanchoe* plant. Such selection can comprise the identification, preferably in an early stage of development, of mildew resistant *Kalanchoe* plants, such as *Oidium kalanchoeae* resistant *Kalanchoe* plants by, for example, hybridization, PCR, ELISA, restriction analysis or Northern/Southern blots thereby facilitating the breeding process of existing and new *Kalanchoe* plants.

The present use is preferably used for the selection of mildew resistant *Kalanchoe* plants selected from the group consisting of *Kalanchoe adelae, Kalanchoe arborescens, Kalanchoe beauverdii, Kalanchoe beharensis, Kalanchoe bentii, Kalanchoe blossfeldiana, Kalanchoe bouvetii, Kalanchoe bracteata, Kalanchoe campanulata, Kalanchoe cre-* nata, Kalanchoe crundallii, Kalanchoe daigremontiana, Kalanchoe delagoensis, Kalanchoe dinklagei, Kalanchoe eriophylla, Kalanchoe farinacea, Kalanchoe fedtschenkoi, Kalanchoe figuereidoi, Kalanchoe flammea, Kalanchoe gastonis, Kalanchoe glaucescens, Kalanchoe gracilipes, Kalanchoe grandidieri, Kalanchoe grandiflora, Kalanchoe hildebrantii, Kalanchoe jongmansii, Kalanchoe kewensis, Kalanchoe laciniata, Kalanchoe laetivirens, Kalanchoe lateritia, Kalanchoe laxiflora, Kalanchoe linearifolia, Kalanchoe longiflora, Kalanchoe luciae, Kalanchoe macrochlamys, Kalanchoe manginii, Kalanchoe marnieriana, Kalanchoe marmorata, Kalanchoe millottii, Kalanchoe miniata, Kalanchoe nyikae, Kalanchoe obtusa, Kalanchoe orgyalis, Kalanchoe peltata, Kalanchoe petitiana, Kalanchoe pinnata, Kalanchoe porphyrocalyx, Kalanchoe prolifera, Kalanchoe pubescens, Kalanchoe pumila, Kalanchoe quartiniana, Kalanchoe rhombopilosa, Kalanchoe robusta, Kalanchoe rolandi, Kalanchoe rosei, Kalanchoe rotundifolia, Kalanchoe schizophylla, Kalanchoe serrata, Kalanchoe sexangularis, Kalanchoe streptantha, Kalanchoe suarezensis, Kalanchoe synsepala, Kalanchoe synsepala f. dissecta, Kalanchoe thyrsflora, Kalanchoe tomentosa, Kalanchoe tubiflora, Kalanchoe uniflora, Kalanchoe velutina and Kalanchoe viguieri; more preferably decorative flowering Kalanchoe plants selected from the group consisting of K. blossfeldiana, K. laciniata, K. rotundifolia, K. aromatica, K. pubescens, K. grandiflora, K. citrina, K. ambolensis, K. faustii, K. schumacherii, K. pritwitzii, K. flammea, K. figueredoi, K. rauhii, K. obtusa, K. pumila, K. marmorata, K. porphyrocalux, K. jongmansii, K. pinnata, K. diagremontiana, K. gracilipes, K. campanulata, K. latisepela, K. coccinea, K. fedtschenkoi, K. tubiflora, K. decumbens, K. manginn, K. orgyalis, K. crenata, K. tomentosa and hybrids thereof.

According to a fifth aspect, the present invention relates to plants, protoplasts or plant parts comprising the present proteins, the present nucleic acid sequences or the present genes. The present plant, protoplasts or plant parts are preferably selected from, or obtained from, a plant selected from the group consisting of Kalanchoe adelae, Kalanchoe arborescens, Kalanchoe beauverdii, Kalanchoe beharensis, Kalanchoe bentii, Kalanchoe blossfeldiana, Kalanchoe bouvetii, Kalanchoe bracteata, Kalanchoe campanulata, Kalanchoe crenata, Kalanchoe crundallii, Kalanchoe daigremontiana, Kalanchoe delagoensis, Kalanchoe dinklagei, Kalanchoe eriophylla, Kalanchoe farinacea, Kalanchoe fedtschenkoi, Kalanchoe figuereidoi, Kalanchoe flammea, Kalanchoe gastonis, Kalanchoe glaucescens, Kalanchoe gracilipes, Kalanchoe grandidieri, Kalanchoe grandiflora, Kalanchoe hildebrantii, Kalanchoe jongmansii, Kalanchoe kewensis, Kalanchoe laciniata, Kalanchoe laetivirens, Kalanchoe lateritia, Kalanchoe laxiflora, Kalanchoe linearifolia, Kalanchoe longiflora, Kalanchoe luciae, Kalanchoe macrochlamys, Kalanchoe manginii, Kalanchoe marnieriana, Kalanchoe marmorata, Kalanchoe Kalanchoe miniata, Kalanchoe nyikae, Kalanchoe obtusa, Kalanchoe orgyalis, Kalanchoe peltata, Kalanchoe petitiana, Kalanchoe pinnata, Kalanchoe porphyrocalyx, Kalanchoe prolifera, Kalanchoe pubescens, Kalanchoe pumila, Kalanchoe quartiniana, Kalanchoe rhombopilosa, Kalanchoe robusta, Kalanchoe rolandi, Kalanchoe rosei, Kalanchoe rotundifolia, Kalanchoe schizophylla, Kalanchoe serrata, Kalanchoe sexangularis, Kalanchoe streptantha, Kalanchoe suarezensis, Kalanchoe synsepala, Kalanchoe synsepala f. dissecta, Kalanchoe thyrsiflora, Kalanchoe tomentosa, Kalanchoe tubiflora, Kalanchoe uniflora, Kalanchoe velutina and Kalanchoe viguieri; preferably decorative flowering Kalanchoe plants selected from the group consisting of K. blossfeldiana, K. laciniata, K. rotundifolia, K. aromatica, K. pubescens, K. grandiflora, K. citrina, K. ambolensis, K. faustii, K. schumacherii, K. pritwitzii, K. flammea, K. figueredoi, K. rauhii, K. obtusa, K. pumila, K. marmorata, K. porphyrocalux, K. jongmansii, K. pinnata, K. diagremontiana, K. gracilipes, K. campanulata, K. latisepela, K. coccinea, K. fedtschenkoi, K. tubiflora, K. decumbens, K. manginn, K. orgyalis, K. crenata, K. tomentosa and hybrids thereof.

BRIEF DESCRIPTION OF THE DRAWINGS

The present invention will be further detailed in the example below of especially preferred embodiments of the present invention. In the example, reference is made to figures wherein.

DETAILED DESCRIPTION

EXAMPLE

An *Oidium kalanchoeae* mildew resistant *Kalanchoe blossfeldiana* parent plant of which representative seeds were deposited at NCIMB Ferguson Building, Craibstone Estate, Bucksburn, Aberdeen AB21 9YA, United Kingdom under deposit number NCIMB 42379 on Mar. 2, 2015, was crossed with a mildew susceptible *Kalanchoe blossfeldiana* plant and a segregating progeny was obtained. Progeny was assayed for *Oidium kalanchoeae* resistance by infecting plants of approximately 4 weeks old with *Oidium kalanchoeae*. Subsequently, the infected plants were grown for approximately 4 weeks under the following conditions:

temperature: day 20° C./night 18° C.;

relative humidity: day 60%/night 80%;

day length: 20 hours (artificial light with an intensity between 1000 and 2000 lux).

Then the plants were visually scored for mildew susceptibility/resistance on a scale of 1 to 9 whereby 1 denoted completely mildew susceptible and 9 completely mildew resistant (no visible infection).

Figure 1:
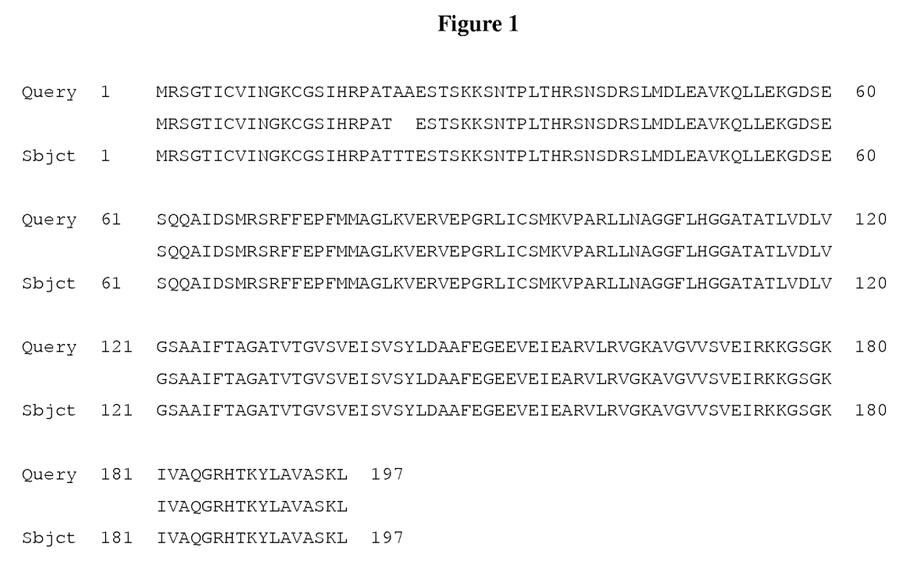
FIG. 1: shows an alignment of a thioesterase protein according to the present invention providing mildew resistance (upper sequence, SEQ ID No. 2) and the thioesterase protein of SEQ ID No. 1 (bottom sequence). The consensus sequence between the two proteins (SEQ ID No. 9) is shown in the middle line.

Analysis of the progeny showed that the observed mildew resistant phenotype correlated with two nucleotide substitutions at positions 64 and 67 of the coding sequence of a gene encoding a thioesterase protein or thioesterase-like protein. As depicted in FIG. 1, both nucleotide substitutions resulted in amino acid substitutions in the N-terminal region of the thioesterase protein or thioesterase-like protein.

Figure 2:
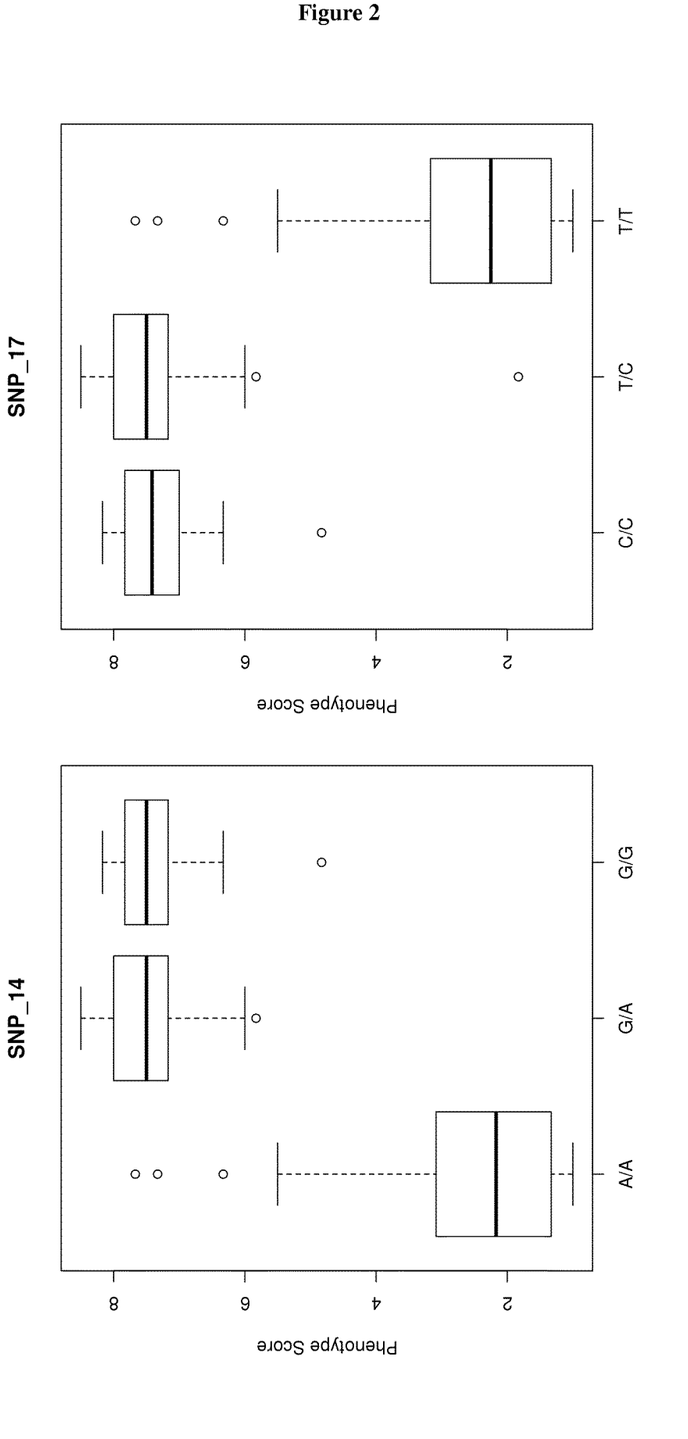
FIG. 2: shows a boxplot of the present mildew resistance in relation to the nucleotide sequences found at position at positions 64 (SNP_14) and 67 (SNP_17) of SEQ ID No. 3 in homozygous and heterozygous form. For position 67, the non-coding nucleotides are shown, i.e. C/C; T/C and T/T instead of the coding nucleotides G/G; A/G; A/A, respectively.

The analysis of the mildew phenotype in the above segregating population is summarized in Table 1 below and FIG. 2.

TABLE 1

Analysis of a segregating population of the present mildew resistance phenotype wherein 1 denotes minimal mildew resistance or the absence thereof and 9 denotes maximal mildew resistance.

| Plant | Phenotype score | SNP_14 | SNP_17_RC |
|---|---|---|---|
| Ka-SxM-100 | 1.00 | A/A | T/T |
| Ka-SxM-084 | 1.00 | A/A | T/T |
| Ka-SxM-024 | 1.00 | A/A | T/T |
| Ka-SxM-064 | 1.00 | A/A | T/T |
| Ka-SxM-073 | 1.17 | A/A | T/T |
| Ka-SxM-126 | 1.17 | A/A | T/T |
| Ka-SxM-004 | 1.17 | A/A | T/T |
| Ka-SxM-086 | 1.17 | A/A | T/T |
| Ka-SxM-079 | 1.17 | A/A | T/T |
| Ka-SxM-026 | 1.33 | A/A | T/T |
| Ka-SxM-020 | 1.33 | A/A | T/T |
| Ka-SxM-136 | 1.33 | A/A | T/T |
| Ka-SxM-069 | 1.33 | A/A | T/T |
| Ka-SxM-078 | 1.33 | A/A | T/T |
| Ka-SxM-087 | 1.33 | A/A | T/T |
| Ka-SxM-072 | 1.33 | A/A | T/T |
| Ka-SxM-027 | 1.50 | A/A | T/T |
| Ka-SxM-081 | 1.83 | A/A | T/C |
| Ka-SxM-012 | 1.83 | A/A | T/T |
| Ka-SxM-062 | 1.83 | A/A | T/T |
| Ka-SxM-044 | 2.00 | A/A | T/T |
| Ka-SxM-052 | 2.17 | A/A | T/T |
| Ka-SxM-082 | 2.33 | A/A | T/T |
| Ka-SxM-092 | 2.50 | A/A | T/T |
| Ka-SxM-061 | 2.50 | A/A | T/T |
| Ka-SxM-075 | 2.83 | A/A | T/T |
| Ka-SxM-050 | 3.00 | A/A | T/T |
| Ka-SxM-090 | 3.00 | A/A | T/T |
| Ka-SxM-053 | 3.00 | A/A | T/T |
| Ka-SxM-113 | 3.00 | A/A | T/T |
| Ka-SxM-008 | 3.00 | A/A | T/T |
| Ka-SxM-080 | 3.00 | A/A | T/T |
| Ka-SxM-028 | 3.17 | A/A | T/T |
| Ka-SxM-013 | 3.50 | A/A | T/T |
| Ka-SxM-037 | 3.50 | A/A | T/T |
| Ka-SxM-022 | 4.00 | A/A | T/T |
| Ka-SxM-068 | 4.83 | A/A | T/T |
| Ka-SxM-046 | 4.83 | G/G | C/C |
| Ka-SxM-030 | 5.17 | A/A | T/T |
| Ka-SxM-014 | 5.33 | A/A | T/T |
| Ka-SxM-106 | 5.50 | A/A | T/T |
| Ka-SxM-060 | 5.67 | Undetermined | Undetermined |
| Ka-SxM-066 | 5.83 | G/A | T/C |
| Ka-SxM-114 | 6.00 | G/A | T/C |
| Ka-SxM-009 | 6.33 | A/A | T/T |
| Ka-SxM-041 | 6.33 | G/G | C/C |
| Ka-SxM-038 | 6.83 | G/G | C/C |
| Ka-SxM-065 | 7.00 | G/A | T/C |
| Ka-SxM-067 | 7.00 | G/A | T/C |
| Ka-SxM-029 | 7.00 | G/A | T/C |
| Ka-SxM-007 | 7.00 | G/A | T/C |
| Ka-SxM-049 | 7.17 | G/A | T/C |
| Ka-SxM-051 | 7.17 | G/A | T/C |
| Ka-SxM-005 | 7.17 | G/G | C/C |
| Ka-SxM-040 | 7.17 | G/A | T/C |
| Ka-SxM-033 | 7.33 | G/A | T/C |
| Ka-SxM-074 | 7.33 | G/G | C/C |
| Ka-SxM-019 | 7.33 | G/A | T/C |
| Ka-SxM-094 | 7.33 | G/A | T/C |
| Ka-SxM-139 | 7.33 | A/A | T/T |
| Ka-SxM-056 | 7.33 | G/G | C/C |
| Ka-SxM-042 | 7.50 | G/A | T/C |
| Ka-SxM-138 | 7.50 | G/A | T/C |
| Ka-SxM-077 | 7.50 | G/G | C/C |
| Ka-SxM-054 | 7.50 | G/A | T/C |
| Ka-SxM-001 | 7.67 | G/G | C/C |
| Ka-SxM-018 | 7.67 | G/A | T/C |
| Ka-SxM-034 | 7.67 | Undetermined | T/C |
| Ka-SxM-071 | 7.67 | A/A | T/T |
| Ka-SxM-057 | 7.83 | G/G | C/C |
| Ka-SxM-058 | 7.83 | G/G | Undetermined |
| Ka-SxM-036 | 7.83 | G/G | C/C |
| Ka-SxM-045 | 7.83 | G/G | C/C |
| Ka-SxM-117 | 7.83 | G/A | T/C |
| Ka-SxM-117 | 7.83 | G/A | T/C |
| Ka-SxM-017 | 8.00 | G/A | T/C |
| Ka-SxM-089 | 8.00 | G/A | T/C |
| Ka-SxM-003 | 8.00 | G/A | T/C |
| Ka-SxM-043 | 8.00 | G/A | T/C |
| Ka-SxM-076 | 8.00 | G/A | T/C |
| Ka-SxM-023 | 8.00 | G/A | T/C |
| Ka-SxM-031 | 8.17 | G/G | C/C |
| Ka-SxM-035 | 8.33 | G/A | T/C |
| Ka-SxM-032 | 8.33 | G/A | T/C |
| Ka-SxM-048 | 8.50 | G/A | T/C |

The invention claimed is:

1. A protein having the sequence of SEQ ID NO: 2.

2. A method for obtaining a *Kalanchoe* plant that is resistant to mildew, comprising introducing a nucleic acid sequence encoding SEQ ID NO: 2 into a *Kalanchoe* plant that is susceptible to mildew.

3. The method according to claim 2, wherein the *Kalanchoe* plant is selected from the group consisting of *Kalanchoe adelae, Kalanchoe arborescens, Kalanchoe beauverdii, Kalanchoe beharensis, Kalanchoe bentii, Kalanchoe blossfeldiana, Kalanchoe bouvetii, Kalanchoe bracteata, Kalanchoe campanulata, Kalanchoe crenata, Kalanchoe crundallii, Kalanchoe daigremontiana, Kalanchoe delagoensis, Kalanchoe dinklagei, Kalanchoe eriophylla, Kalanchoe farinacea, Kalanchoe fedtschenkoi, Kalanchoe figuereidoi, Kalanchoe flammea, Kalanchoe gastonis, Kalanchoe glaucescens, Kalanchoe gracilipes, Kalanchoe grandidieri, Kalanchoe grandiflora, Kalanchoe hildebrantii, Kalanchoe jongmansii, Kalanchoe kewensis, Kalanchoe laciniata, Kalanchoe laetivirens, Kalanchoe lateritia, Kalanchoe laxiflora, Kalanchoe linearifolia, Kalanchoe longiflora, Kalanchoe luciae, Kalanchoe macrochlamys, Kalanchoe manginii, Kalanchoe marnieriana, Kalanchoe marmorata, Kalanchoe millottii, Kalanchoe miniata, Kalanchoe nyikae, Kalanchoe obtusa, Kalanchoe orgyalis, Kalanchoe peltata, Kalanchoe petitiana, Kalanchoe pinnata, Kalanchoe porphyrocalyx, Kalanchoe prolifera, Kalanchoe pubescens, Kalanchoe pumila, Kalanchoe quartiniana, Kalanchoe rhombopilosa, Kalanchoe robusta, Kalanchoe rolandi, Kalanchoe rosei, Kalanchoe rotundifolia, Kalanchoe schizophylla, Kalanchoe serrata, Kalanchoe sexangularis, Kalanchoe streptantha, Kalanchoe suarezensis, Kalanchoe synsepala, Kalanchoe synsepala f. dissecta, Kalanchoe thyrsiflora, Kalanchoe tomentosa, Kalanchoe tubiflora, Kalanchoe uniflora, Kalanchoe velutina, Kalanchoe viguieri*, and hybrids thereof.

4. The method according to claim 2, wherein the resistance to mildew comprises resistance to the mildew pathogen *Oidium kalanchoeae*.

5. A *Kalanchoe* plant produced from the method according to claim 2, wherein the plant comprises in its genome a nucleic acid sequence encoding a protein having the sequence of SEQ ID NO: 2 and exhibits resistance to mildew.

6. A seed, tissue, or plant part of the *Kalanchoe* plant according to claim 5, wherein the seed, tissue, or plant part comprises in its genome a nucleic acid sequence encoding a protein that has the sequence of SEQ ID NO: 2.

7. A *Kalanchoe* plant comprising a protein comprising the sequence of SEQ ID NO: 2 and exhibiting resistance to mildew.

8. The *Kalanchoe* plant according to claim 7, wherein the *Kalanchoe* plant is selected from the group consisting of *Kalanchoe adelae, Kalanchoe arborescens, Kalanchoe beauverdii, Kalanchoe beharensis, Kalanchoe bentii, Kalanchoe blossfeldiana, Kalanchoe bouvetii, Kalanchoe bracteata, Kalanchoe campanulata, Kalanchoe crenata, Kalanchoe crundallii, Kalanchoe daigremontiana, Kalanchoe delagoensis, Kalanchoe dinklagei, Kalanchoe eriophylla, Kalanchoe farinacea, Kalanchoe fedtschenkoi, Kalanchoe figuereidoi, Kalanchoe flammea, Kalanchoe gastonis, Kalanchoe glaucescens, Kalanchoe gracilipes, Kalanchoe grandidieri, Kalanchoe grandiflora, Kalanchoe hildebrantii, Kalanchoe jongmansii, Kalanchoe kewensis, Kalanchoe laciniata, Kalanchoe laetivirens, Kalanchoe lateritia, Kalanchoe laxiflora, Kalanchoe linearifolia, Kalanchoe longiflora, Kalanchoe luciae, Kalanchoe macrochlamys, Kalanchoe manginii, Kalanchoe marnieriana, Kalanchoe marmorata, Kalanchoe millottii, Kalanchoe miniata, Kalanchoe nyikae, Kalanchoe obtusa, Kalanchoe orgyalis, Kalanchoe peltata, Kalanchoe petitiana, Kalanchoe pinnata, Kalanchoe porphyrocalyx, Kalanchoe prolifera, Kalanchoe pubescens, Kalanchoe pumila, Kalanchoe quartiniana, Kalanchoe rhombopilosa, Kalanchoe robusta, Kalanchoe rolandi, Kalanchoe rosei, Kalanchoe rotundifolia, Kalanchoe schizophylla, Kalanchoe serrata, Kalanchoe sexangularis, Kalanchoe streptantha, Kalanchoe suarezensis, Kalanchoe synsepala, Kalanchoe synsepala f. dissecta, Kalanchoe thyrsiflora, Kalanchoe tomentosa, Kalanchoe tubiflora, Kalanchoe uniflora, Kalanchoe velutina, Kalanchoe viguieri*, and hybrids thereof.

9. A seed, tissue, or plant part of the *Kalanchoe* plant according to claim 7, wherein the seed, tissue, or plant part comprises SEQ ID NO: 2.

* * * * *

UNITED STATES PATENT AND TRADEMARK OFFICE
CERTIFICATE OF CORRECTION

PATENT NO.        : 10,815,466 B2
APPLICATION NO.   : 15/553199
DATED             : October 27, 2020
INVENTOR(S)       : Izaak Johannes Vlielander et al.

It is certified that error appears in the above-identified patent and that said Letters Patent is hereby corrected as shown below:

On the Title Page

Under ABSTRACT "9 Claims, 2 Drawing Sheets" should read:
--5 Claims, 2 Drawing Sheets-- as attached.

In the Claims

Column 15, Line 19-Column 16, Lines 18-60, should read:
-- 1. A method for obtaining a *Kalanchoe* plant that is resistant to mildew, comprising introducing a nucleic acid sequence encoding SEQ ID NO: 2 into a *Kalanchoe* plant that is susceptible to mildew.
2. The method according to claim 1, wherein the *Kalanchoe* plant is selected from the group consisting of *Kalanchoe adelae, Kalanchoe arborescens, Kalanchoe beauverdii, Kalanchoe beharensis, Kalanchoe bentii, Kalanchoe blossfeldiana, Kalanchoe bouvetii, Kalanchoe bracteata, Kalanchoe campanulata, Kalanchoe crenata, Kalanchoe crundallii, Kalanchoe daigremontiana, Kalanchoe delagoensis, Kalanchoe dinklagei, Kalanchoe eriophylla, Kalanchoe farinacea, Kalanchoe fedtschenkoi, Kalanchoe figuereidoi, Kalanchoe flammea, Kalanchoe gastonis, Kalanchoe glaucescens, Kalanchoe gracilipes, Kalanchoe grandidieri, Kalanchoe grandiflora, Kalanchoe hildebrantii, Kalanchoe jongmansii, Kalanchoe kewensis, Kalanchoe laciniata, Kalanchoe laetivirens, Kalanchoe lateritia, Kalanchoe laxiflora, Kalanchoe linearifolia, Kalanchoe longiflora, Kalanchoe luciae, Kalanchoe macrochlamys, Kalanchoe manginii, Kalanchoe marnieriana, Kalanchoe marmorata, Kalanchoe millottii, Kalanchoe miniata, Kalanchoe nyikae, Kalanchoe obtusa, Kalanchoe orgyalis, Kalanchoe peltata, Kalanchoe petitiana, Kalanchoe pinnata, Kalanchoe porphyrocalyx, Kalanchoe prolifera, Kalanchoe pubescens, Kalanchoe pumila, Kalanchoe quartiniana, Kalanchoe rhombopilosa, Kalanchoe robusta, Kalanchoe rolandi, Kalanchoe rosei, Kalanchoe rotundifolia, Kalanchoe schizophylla, Kalanchoe serrata, Kalanchoe sexangularis, Kalanchoe streptantha, Kalanchoe suarezensis, Kalanchoe synsepala, Kalanchoe synsepala f. dissecta, Kalanchoe thyrsiflora, Kalanchoe tomentosa, Kalanchoe tubiflora, Kalanchoe uniflora, Kalanchoe velutina, Kalanchoe viguieri*, and hybrids thereof.
3. The method according to claim 1, wherein the resistance to mildew comprises resistance to the mildew pathogen *Oidium kalanchoeae.*

Signed and Sealed this
Fifth Day of October, 2021

Drew Hirshfeld
*Performing the Functions and Duties of the
Under Secretary of Commerce for Intellectual Property and
Director of the United States Patent and Trademark Office*

4. A *Kalanchoe* plant produced from the method according to claim 1, wherein the plant comprises in its genome a nucleic acid sequence encoding a protein having the sequence of SEQ ID NO: 2 and exhibits resistance to mildew.

5. A seed, tissue, or plant part of the *Kalanchoe* plant according to claim 4, wherein the seed, tissue, or plant part comprises in its genome a nucleic acid sequence encoding a protein that has the sequence of SEQ ID NO: 2." --

(12) United States Patent
Vlielander et al.

(10) Patent No.: US 10,815,466 B2
(45) Date of Patent: Oct. 27, 2020

(54) MILDEW RESISTANCE GENE IN KALANCHOE

(71) Applicant: Dümmen Group B.V., De Lier (NL)

(72) Inventors: Izaak Johannes Vlielander, De Lier (NL); Chunting Lang, De Lier (NL); Paulus Cornelis Maris, De Lier (NL); Roger Adrianus Peeters, Weert (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/553,199

(22) PCT Filed: Feb. 29, 2016

(86) PCT No.: PCT/EP2016/054220
§ 371 (c)(1),
(2) Date: Aug. 24, 2017

(87) PCT Pub. No.: WO2016/139178
PCT Pub. Date: Sep. 9, 2016

(65) Prior Publication Data
US 2018/0037875 A1    Feb. 8, 2018

(30) Foreign Application Priority Data
Mar. 4, 2015  (EP) .................................... 15157519

(51) Int. Cl.
*C12N 15/82* (2006.01)
*C12N 9/16* (2006.01)

(52) U.S. Cl.
CPC ........... *C12N 9/16* (2013.01); *C12N 15/8282* (2013.01); *C12Y 301/02* (2013.01)

(58) Field of Classification Search
CPC ........................................................ C12N 9/16
USPC ..................................................... 800/279
See application file for complete search history.

(56) References Cited

U.S. PATENT DOCUMENTS

| | | | |
|---|---|---|---|
| PP6,878 P | 6/1989 | Finger | |
| PP13,355 P2 | 12/2002 | Rosborg | |
| PP18,030 P3 * | 9/2007 | Jepsen | A01H 6/32 |
| 2007/0061916 A1 * | 3/2007 | Kovalic | C07K 14/415 |
| | | | 800/278 |

FOREIGN PATENT DOCUMENTS

NL          2013042 A      11/2014

OTHER PUBLICATIONS

GenBank Accession No. KDP24210.1 (2014).*
Third Party Observation submitted in European Patent Application No. 15157519.8, dated Jan. 6, 2020.*
Database UniProt [Online] Sep. 3, 2014 (Sep. 3, 2014), "SubName: Full=Uncharacterized protein {ECO:0000313:EMBL:KDP24210. 1};" XP002743885, 1,2, 7-11, 13-16,18 retrieved from EBI accession No. UNIPROT: AOA067JW66 Database accession No. AOA067JW66 sequence.
Song et al., "Overexpresion of a wheat stearoyl-ACP desaturase (SACPD) gene TaSSI2 in *Arabidopsis* ssi2 mutant compromise its resistance to powdery mildew", Gene, 2013, pp. 220-227, vol. 524.
Tang et al., "Mutations in LACS2, a Long-Chain Acyl-Coenzyme A Synthetase, Enhance Susceptibility to Avirulent Pseudomonas syringae But Confer Resistance to Botrytis cinerea in *Arabidopsis*", Plant Physiology, 2007, pp. 1093-1103, vol. 144.
Third Party Observations submitted in European Patent Application No. 15157519.8, dated Jan. 6, 2020.

* cited by examiner

*Primary Examiner* — Li Zheng
(74) *Attorney, Agent, or Firm* — The Webb Law Firm (57) ABSTRACT

Provided herein are proteins capable of providing a mildew resistant phenotype, or mildew resistance, to plants belonging to the *Kalanchoe* genus. Also provided herein are nucleic acid sequences, or cDNA sequences, and genes encoding the present proteins. Further provided herein are methods using the proteins, nucleic acid sequences and genes for selecting mildew resistant *Kalanchoe* plants, such as *Oidium kalanchoeae* resistant *Kalanchoe* plants, and to generate mildew resistant *Kalanchoe* plants, such as *Oidium kalanchoeae* resistant *Kalanchoe* plants, comprising the present proteins, mRNA forms of the present cDNAs or the present genes.

5 Claims, 2 Drawing Sheets
Specification includes a Sequence Listing.

SEQUENCE LISTING

<160> NUMBER OF SEQ ID NOS: 9

<210> SEQ ID NO 1
<211> LENGTH: 197
<212> TYPE: PRT
<213> ORGANISM: Kalanchoe blossfeldiana

<400> SEQUENCE: 1

```
Met Arg Ser Gly Thr Ile Cys Val Ile Asn Gly Lys Cys Gly Ser Ile
1               5                   10                  15

His Arg Pro Ala Thr Thr Thr Glu Ser Thr Ser Lys Lys Ser Asn Thr
            20                  25                  30

Pro Leu Thr His Arg Ser Asn Ser Asp Arg Ser Leu Met Asp Leu Glu
        35                  40                  45

Ala Val Lys Gln Leu Leu Glu Lys Gly Asp Ser Glu Ser Gln Gln Ala
    50                  55                  60

Ile Asp Ser Met Arg Ser Arg Phe Phe Glu Pro Phe Met Met Ala Gly
65                  70                  75                  80
```

Leu Lys Val Glu Arg Val Glu Pro Gly Arg Leu Ile Cys Ser Met Lys
                85                  90                  95

Val Pro Ala Arg Leu Leu Asn Ala Gly Gly Phe Leu His Gly Gly Ala
            100                 105                 110

Thr Ala Thr Leu Val Asp Leu Val Gly Ser Ala Ala Ile Phe Thr Ala
            115                 120                 125

Gly Ala Thr Val Thr Gly Val Ser Val Glu Ile Ser Val Ser Tyr Leu
            130                 135                 140

Asp Ala Ala Phe Glu Gly Glu Val Glu Ile Glu Ala Arg Val Leu
145                 150                 155                 160

Arg Val Gly Lys Ala Val Gly Val Val Ser Val Glu Ile Arg Lys Lys
                165                 170                 175

Gly Ser Gly Lys Ile Val Ala Gln Gly Arg His Thr Lys Tyr Leu Ala
                180                 185                 190

Val Ala Ser Lys Leu
                195

<210> SEQ ID NO 2
<211> LENGTH: 197
<212> TYPE: PRT
<213> ORGANISM: Kalanchoe blossfeldiana

<400> SEQUENCE: 2

Met Arg Ser Gly Thr Ile Cys Val Ile Asn Gly Lys Cys Gly Ser Ile
1               5                   10                  15

His Arg Pro Ala Thr Ala Ala Glu Ser Thr Ser Lys Lys Ser Asn Thr
                20                  25                  30

Pro Leu Thr His Arg Ser Asn Ser Asp Arg Ser Leu Met Asp Leu Glu
            35                  40                  45

Ala Val Lys Gln Leu Leu Glu Lys Gly Asp Ser Glu Ser Gln Gln Ala
        50                  55                  60

Ile Asp Ser Met Arg Ser Arg Phe Phe Glu Pro Phe Met Met Ala Gly
65                  70                  75                  80

Leu Lys Val Glu Arg Val Glu Pro Gly Arg Leu Ile Cys Ser Met Lys
                85                  90                  95

Val Pro Ala Arg Leu Leu Asn Ala Gly Gly Phe Leu His Gly Gly Ala
            100                 105                 110

Thr Ala Thr Leu Val Asp Leu Val Gly Ser Ala Ala Ile Phe Thr Ala
            115                 120                 125

Gly Ala Thr Val Thr Gly Val Ser Val Glu Ile Ser Val Ser Tyr Leu
            130                 135                 140

Asp Ala Ala Phe Glu Gly Glu Val Glu Ile Glu Ala Arg Val Leu
145                 150                 155                 160

Arg Val Gly Lys Ala Val Gly Val Val Ser Val Glu Ile Arg Lys Lys
                165                 170                 175

Gly Ser Gly Lys Ile Val Ala Gln Gly Arg His Thr Lys Tyr Leu Ala
                180                 185                 190

Val Ala Ser Lys Leu
                195

<210> SEQ ID NO 3
<211> LENGTH: 594
<212> TYPE: DNA
<213> ORGANISM: Kalanchoe blossfeldiana

<400> SEQUENCE: 3

```
atgagatccg gacgatttg tgtaataaac ggaaagtgtg aagcatcca caggccagca    60
acaacaacag aatctacatc gaaaaaatcg aacacrcctt tgactcatcg atcgaactcc   120
gaccggtctc tgatggatct ggaagcagtg aagcagttgc tggagaaggg agacagcgaa   180
agccagcaag cgatcgactc gatgcgctca cggttcttcg agccgttcat gatggcaggg   240
ctgaaggtgg agagggtgga gccagggagg ctgatctgca gcatgaaggt gccggcgcgg   300
ctgctgaacg cgggagggtt cctgcacggg ggagcgacgg cgacgctggt ggatctggtg   360
ggmtcggcgg cgatattcac ggcggggcg acggtgacgg gcgtgtcggt ggagatcagc    420
gtgtcgtatc tggacgcggc gttcgagggg gaggaggtgg agatcgaggc gcgggtgctg   480
agggtgggga agcggtggg ggtcgtcagc gttgagattc ggaagaaggg ragtgggaag    540
attgtggcgc aggggcggca caccaagtat ctggctgtgg ccagcaagct gtag         594
```

<210> SEQ ID NO 4
<211> LENGTH: 594
<212> TYPE: DNA
<213> ORGANISM: Kalanchoe blossfeldiana

<400> SEQUENCE: 4

```
atgagatccg gacgatttg tgtaataaac ggaaagtgtg aagcatcca caggccagca    60
acagcarcag aatctacatc gaaaaaatcg aacacrcctt tgactcatcg atcgaactcc   120
gaccggtctc tgatggatct ggaagcagtg aagcagttgc tggagaaggg agacagcgaa   180
agccagcaag cgatcgactc gatgcgctca cggttcttcg agccgttcat gatggcaggg   240
ctgaaggtgg agagggtgga gccagggagg ctgatctgca gcatgaaggt gccggcgcgg   300
ctgctgaacg cgggagggtt cctgcacggg ggagcgacgg cgacgctggt ggatctggtg   360
ggmtcggcgg cgatattcac ggcggggcg acggtgacgg gcgtgtcggt ggagatcagc    420
gtgtcgtatc tggacgcggc gttcgagggg gaggaggtgg agatcgaggc gcgggtgctg   480
agggtgggga agcggtggg ggtcgtcagc gttgagattc ggaagaaggg ragtgggaag    540
attgtggcgc aggggcggca caccaagtat ctggctgtgg ccagcaagct gtag         594
```

<210> SEQ ID NO 5
<211> LENGTH: 594
<212> TYPE: DNA
<213> ORGANISM: Kalanchoe blossfeldiana

<400> SEQUENCE: 5

```
atgagatccg gacgatttg tgtaataaac ggaaagtgtg aagcatcca caggccagca    60
acarcagcag aatctacatc gaaaaaatcg aacacrcctt tgactcatcg atcgaactcc   120
gaccggtctc tgatggatct ggaagcagtg aagcagttgc tggagaaggg agacagcgaa   180
agccagcaag cgatcgactc gatgcgctca cggttcttcg agccgttcat gatggcaggg   240
ctgaaggtgg agagggtgga gccagggagg ctgatctgca gcatgaaggt gccggcgcgg   300
ctgctgaacg cgggagggtt cctgcacggg ggagcgacgg cgacgctggt ggatctggtg   360
ggmtcggcgg cgatattcac ggcggggcg acggtgacgg gcgtgtcggt ggagatcagc    420
gtgtcgtatc tggacgcggc gttcgagggg gaggaggtgg agatcgaggc gcgggtgctg   480
agggtgggga agcggtggg ggtcgtcagc gttgagattc ggaagaaggg ragtgggaag    540
attgtggcgc aggggcggca caccaagtat ctggctgtgg ccagcaagct gtag         594
```

<210> SEQ ID NO 6
<211> LENGTH: 594

<212> TYPE: DNA
<213> ORGANISM: Kalanchoe blossfeldiana

<400> SEQUENCE: 6

```
atgagatccg ggacgatttg tgtaataaac ggaaagtgtg gaagcatcca caggccagca      60
acagcagcag aatctacatc gaaaaaatcg aacacrccttt tgactcatcg atcgaactcc    120
gaccggtctc tgatggatct ggaagcagtg aagcagttgc tggagaaggg agacagcgaa    180
agccagcaag cgatcgactc gatgcgctca cggttcttcg agccgttcat gatggcaggg    240
ctgaaggtgg agagggtgga gccagggagg ctgatctgca gcatgaaggt gccggcgcgg    300
ctgctgaacg cgggagggtt cctgcacggg ggagcgacgg cgacgctggt ggatctggtg    360
ggmtcggcgg cgatattcac ggcggggggcg acggtgacgg gcgtgtcggt ggagatcagc    420
gtgtcgtatc tggacgcggc gttcgagggg gaggaggtgg agatcgaggc gcgggtgctg    480
agggtgggga aggcggtggg ggtcgtcagc gttgagattc ggaagaaggg ragtgggaag    540
attgtggcgc aggggcggca caccaagtat ctggctgtgg ccagcaagct gtag          594
```

<210> SEQ ID NO 7
<211> LENGTH: 8
<212> TYPE: PRT
<213> ORGANISM: Kalanchoe blossfeldiana

<400> SEQUENCE: 7

Pro Ala Thr Ala Ala Glu Ser Thr
1               5

<210> SEQ ID NO 8
<211> LENGTH: 8
<212> TYPE: PRT
<213> ORGANISM: Kalanchoe blossfeldiana

<400> SEQUENCE: 8

Pro Ala Thr Thr Thr Glu Ser Thr
1               5

<210> SEQ ID NO 9
<211> LENGTH: 195
<212> TYPE: PRT
<213> ORGANISM: Artificial Sequence
<220> FEATURE:
<223> OTHER INFORMATION: Consensus thioesterase sequence

<400> SEQUENCE: 9

Met Arg Ser Gly Thr Ile Cys Val Ile Asn Gly Lys Cys Gly Ser Ile
1               5                   10                  15

His Arg Pro Ala Thr Glu Ser Thr Ser Lys Lys Ser Asn Thr Pro Leu
            20                  25                  30

Thr His Arg Ser Asn Ser Asp Arg Ser Leu Met Asp Leu Glu Ala Val
        35                  40                  45

Lys Gln Leu Leu Glu Lys Gly Asp Ser Glu Ser Gln Gln Ala Ile Asp
    50                  55                  60

Ser Met Arg Ser Arg Phe Phe Glu Pro Phe Met Met Ala Gly Leu Lys
65                  70                  75                  80

Val Glu Arg Val Glu Pro Gly Arg Leu Ile Cys Ser Met Lys Val Pro
                85                  90                  95

Ala Arg Leu Leu Asn Ala Gly Gly Phe Leu His Gly Gly Ala Thr Ala
            100                 105                 110

Thr Leu Val Asp Leu Val Gly Ser Ala Ala Ile Phe Thr Ala Gly Ala

-continued

```
            115                 120                 125
Thr Val Thr Gly Val Ser Val Glu Ile Ser Val Ser Tyr Leu Asp Ala
    130                 135                 140

Ala Phe Glu Gly Glu Glu Val Glu Ile Glu Ala Arg Val Leu Arg Val
145                 150                 155                 160

Gly Lys Ala Val Gly Val Val Ser Val Glu Ile Arg Lys Lys Gly Ser
                165                 170                 175

Gly Lys Ile Val Ala Gln Gly Arg His Thr Lys Tyr Leu Ala Val Ala
            180                 185                 190

Ser Lys Leu
    195
```